(12) United States Patent
Stein et al.

(10) Patent No.: US 8,026,059 B2
(45) Date of Patent: Sep. 27, 2011

(54) TREATMENT RESPONSE IN GENERALIZED SOCIAL PHOBIA

(75) Inventors: Murray B. Stein, San Diego, CA (US); Joel Gelernter, Woodbridge, CT (US)

(73) Assignee: The Regents of the University of California, Oakland, CA (US)

( * ) Notice: Subject to any disclaimer, the term of this patent is extended or adjusted under 35 U.S.C. 154(b) by 374 days.

(21) Appl. No.: 12/279,178

(22) PCT Filed: Feb. 14, 2007

(86) PCT No.: PCT/US2007/062144
§ 371 (c)(1),
(2), (4) Date: Apr. 22, 2009

(87) PCT Pub. No.: WO2007/095580
PCT Pub. Date: Aug. 23, 2007

(65) Prior Publication Data
US 2009/0220971 A1 Sep. 3, 2009

Related U.S. Application Data

(60) Provisional application No. 60/773,488, filed on Feb. 15, 2006.

(51) Int. Cl.
*C12Q 1/68* (2006.01)
(52) U.S. Cl. .......................................................... 435/6
(58) Field of Classification Search ........................ None
See application file for complete search history.

(56) References Cited

U.S. PATENT DOCUMENTS
2005/0165115 A1 7/2005 Murphy et al.

OTHER PUBLICATIONS

Lotrich et al. Am J Pharmacogenomics. 2001: 1(3) 153-164.*
Perna et al. Neuropsychopharmacology (2005) 30, 2230-2235.*
Arias, B. et al., "5-HTTLPR Polymorphism of the Serotonin Transporter Gene Predicts Non-Remission in Major Depression Patients Treated with Citalopram in a 12-Weeks Follow Up Study," Journal of Clinical Psychopharmacology, 2003, pp. 563-567, vol. 23, No. 6.
Durham, L.K. et al., "The Serotonin Transporter Polymorphism, 5HTTLPR, is Associated with a Faster Response Time to Sertraline in an Elderly Population with Major Depressive Disorder," Psychopharmacology, 2004, pp. 525-529, vol. 174.
Kato, M. et al., "Controlled Clinical Comparison of Paroxetine and Fluvoxamine Considering of Serotonin Transporter Promoter Polymorphism," International Clinical Psychopharmacology, 2005, pp. 151-156, vol. 20, No. 3.
Lotrich, F.E. et al., "Polymorphism of the Serotonin Transporter: Implications for the Use of the Selective Serotonin Reuptake Inhibitors," Practical Pharmocogenomics, 2001, pp. 153-164, vol. 1, No. 3.
Murphy, G.M. et al., "Effects of the Serotonin Transporter Gene Promoter Polymorphism on Mirtzapine and Paroxetine Efficacy and Adverse Events in Geriatric Major Depression," Archives of General Psychology, 2004, pp. 1163-1169, vol. 61.
PCT International Search Report and Written Opinion, PCT/US2007/062144, Dec. 12, 2007, 12 pages.
Perna, G. et al., "Antipanic Efficacy of Paroxetine and Polymorphism with the Promoter of the Serotonin Transporter Gene," Neuropsychopharmacology, 2005, pp. 2230-2235, vol. 30.
Pollock, B.G. et al., "Allelic Variation in the Serotonin Transporter Promoter Affects Onset of Paroxetine Treatment in Response in Late-Life Depression," Neuropsychopharmacology, 2000, pp. 587-590, vol. 23, No. 5.
Smeraldi, E. et al., "Polymorphism Within the Promoter of the Serotonin Transporter Gene and Antidepressant Efficacy of Fluvoxamine," Molecular Psychiatry, 1998, pp. 508-511, vol. 3.
Stein, D.J. et al., "Pharmacotherapy for Social Anxiety Disorder," Cochrane Database of Systematic Reviews, 2000, Issue 4, No. CD001206, DOI:10.1002/14651858.CN001206.pub2.
Weizman, A. et al, "Serotonin Transporter Polymorphism and Response to SSRIs in Major Depression and Relevance to Anxiety Disorders and Substance Abuse," Pharmacogenomics, 2000, pp. 335-341, vol. 1, No. 3.
Yoshida, K. et al, "Influence of the Serotonin Transporter Gene-Linked Polymorphic Region on the Antidepressant Response to Fluvoxamine in Japanese Depressed Patients," Progress on Neuro-Psychopharmacology & Biological Psychiatry, 2002, pp. 383-386, vol. 26.
Yu, Yw-Y. et al., "Association Study of the Serotonin Transporter Promoter Polymorphism and Symptomatology and Antidepressant Response in Major Depressive Disorders," Molecular Psychiatry, 2002, pp. 1115-1119, vol. 7.
Zanardi, R. et al., "Factors Affecting Fluvoxamine Antidepressant Activity: Influence of Pindolol and 5-HTTLPR in Delusional and Nondelusional Depression," Biological Psychiatry, 2001, pp. 323-330, vol. 50.

* cited by examiner

*Primary Examiner* — Juliet Switzer
(74) *Attorney, Agent, or Firm* — Fenwick & West LLP

(57) ABSTRACT

This invention generally pertains to the field of psychiatry. In particular, this invention relates to, inter alia, the discovery that a subject's serotonin transporter gene promoter polymorphism genotype can be used to determine the subject's response to certain drug therapies.

19 Claims, 2 Drawing Sheets

TREATMENT RESPONSE IN GENERALIZED SOCIAL PHOBIA

CROSS REFERENCE TO RELATED APPLICATION

This application is the National Stage of International Application No. PCT/US2007/062144, filed Feb. 14, 2007, and claims priority to U.S. Application No. 60/773,488, filed Feb. 15, 2006, both of which are incorporated by reference in their entirety.

This invention was made with Government support of Grant No. MH64122 awarded by the National Institutes of Health. The Government has certain rights in this invention.

FIELD

This invention generally pertains to the field of psychiatry. In particular, this invention relates to, inter alia, the discovery that a subject's serotonin transporter gene promoter polymorphism genotype can be used to determine the subject's response to certain drug therapies.

BACKGROUND

Social anxiety disorder, also known as social phobia, is a common (lifetime prevalence 12%) (Kessler et al., *Arch Gen Psychiatry* 62:593-602, 2005), frequently disabling disorder (Stein and Kean, *Am J Psychiatry* 157:1606-1613, 2000) whose pathophysiology is poorly understood (Charney, *Am J Psychiatry* 161:1-2, 2004). Generalized social anxiety disorder (GSAD) is a more pervasive, chronic, heritable subtype of the disorder with a lifetime prevalence of 4-5% (Schneier, *BMJ* 327:515-516, 2003; Stein and Gorman, *J Psychiatry Neurosci* 26:185-189, 2001). Serotonin reuptake inhibitors (SRIs), which refer to selective serotonin reuptake inhibitors (SSRIs) and norepinephrine-serotonin (or "dual") reuptake inhibitors (NSRIs), are the most widely used, evidence-based treatment for GSAD (Stein et al., *Cochrane Database Syst Rev* CD001206, 2004) but approximately 40% of patients fail to derive an adequate therapeutic effect (Van Ameringen et al., *Expert Opin Pharmacother* 6:819-830, 2005). Explanations for this heterogeneity of response are lacking but could, theoretically, involve individual differences in brain serotonin metabolism. There is currently no existing method for determining the likelihood of a successful response to SRIs in individuals with GSAD. A need exists to determine the likelihood that an individual with GSAD will respond to treatment with SSRIs so that appropriate treatment protocols can be provided to subjects with GSAD. This invention is directed to this and other important ends.

SUMMARY

Figure 1:
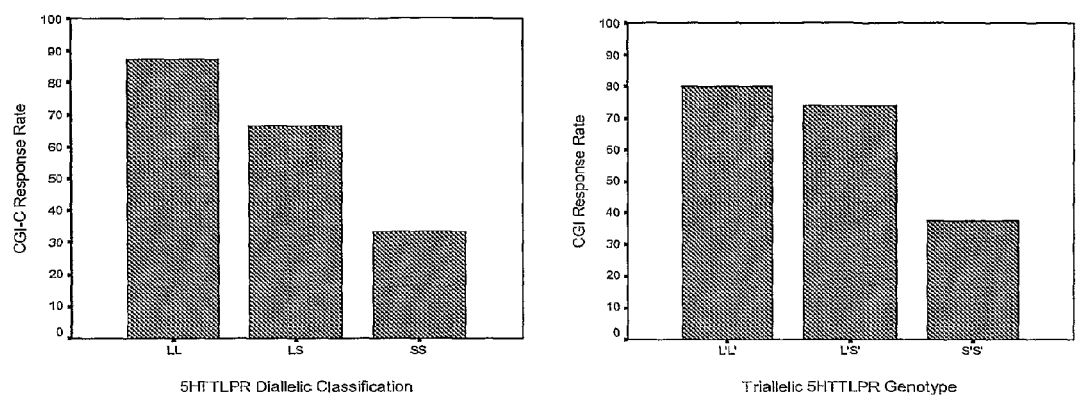
FIG. 1 provides a bar graph showing the SSRI response rate to 12 weeks of SSRI treatment by 5HTTLPR genotype. "ll" represents subjects homozygous for the long variant of the serotonin transporter gene promoter polymorphism; "ls" represents subjects heterozygous for the long variant of the serotonin transporter gene promoter polymorphism; and "ss" represents subjects homozygous for the short variant of the serotonin transporter gene promoter polymorphism.

The present inventors have found that variation in a functional polymorphism known to influence serotonin reuptake is associated with SSRI response in subjects with GSAD. The present invention thus provides, inter alia, methods for predicting response to treatment with a serotonin reuptake inhibitors in a subject diagnosed with generalized social anxiety disorder.

In certain aspects, the present invention provides methods for determining a response profile to treatment with a serotonin reuptake inhibitor in a subject diagnosed with generalized social anxiety disorder. The methods comprise determining the subject's serotonin transporter gene promoter polymorphism genotype. In certain embodiments, a biological sample from a subject will be tested for the presence of the "s" variant of the serotonin transporter gene promoter polymorphism. In certain embodiments, it will be determined whether the subject is homozygous for the long (l) variant of the serotonin transporter gene promoter polymorphism, heterozygous for the long (l) variant of the serotonin transporter gene promoter polymorphism or homozygous for the short (s) variant of the serotonin transporter gene promoter polymorphism.

In certain aspects, the present invention provides methods for determining whether to treat or continue treatment of a subject diagnosed with generalized social anxiety disorder with a serotonin reuptake inhibitor. The methods comprise determining the subject's serotonin transporter gene promoter polymorphism genotype and correlating the subject's serotonin transporter gene promoter polymorphism genotype with a probability of being a positive responder or poor responder to therapy with the serotonin reuptake inhibitor. In certain aspects, the methods further comprise the step of treating the subject with a serotonin reuptake inhibitor. In other aspects, the methods comprise the step of treating the subject with a drug other than a serotonin reuptake inhibitor.

In certain aspects, the present invention provides methods for optimizing therapeutic efficacy of treatment in a subject diagnosed with generalized social anxiety disorder comprising determining the subject's serotonin transporter gene promoter polymorphism genotype, correlating the subject's serotonin transporter gene promoter polymorphism genotype with a probability of being a positive responder or poor responder to therapy with the serotonin reuptake inhibitor, and selecting a drug for treatment based on the correlation.

DETAILED DESCRIPTION OF ILLUSTRATIVE EMBODIMENTS

This invention pertains to the discovery that a subject's serotonin transporter gene promoter polymorphism genotype can be used to determine the likelihood or probability that the subject will respond to SRI therapy for the treatment of GSAD in the subject. In particular, it has been discovered that the presence of one or more copies of the "s" allele is associated with poorer response to SSRI's in subjects suffering from GSAD. The human serotonin transporter 5-HTT is encoded by a single gene (SLC6A4) on chromosome 17q11.1-q12. The serotonin transporter gene promoter polymorphism refers to a functional polymorphism in the promoter region of the serotonin transporter gene. The promoter region is the transcriptional control region approximately 1 kb upstream of the 5-HTT coding sequence. The polymorphism consists of a 44 base pair insertion or deletion ranging from base pair −1.212. to base pair −1.255. The variant comprising the 44 base pair insertion is referred to as the long variant whereas the variant comprising the 44 base pair deletion is referred to as the short variant. The long and short variants of the 5-HTT gene-linked polymorphic region is referred to as 5-HTTLPR. Subjects that are homozygous for the "s" allele, i.e., for the 44 base pair deletion, are characterized as having a "ss" genotype. Subjects that are heterozygous for the "s" allele or alternatively, heterozygous for the "l" allele are characterized as having a "ls" or "sl" genotype Subjects that are homozygous for the "l" allele are characterized as having a "ll" genotype.

As used herein, the phrase "determining the subject's serotonin transporter gene promoter polymorphism genotype" refers to determining both alleles of the serotonin transporter gene promoter polymorphism (5HTTLPR) genotype. In certain embodiments, it will be determined whether a subject is homozygous for the "l" or "s" variant or is heterozygous.

The phrase "correlating the subject's serotonin transporter gene promoter polymorphism genotype with a probability of being a positive responder or poor responder to therapy," refers to making a determination based on a subject's 5 HTTLPR polymorphism genotype as to whether the subject is more likely to be a positive or poor responder to therapy with SRIs. As provided herein, a subject having one or more "s" variant of the 5 HTTLPR polymorphism will be more likely to be a poor responder to therapy with a SRI as compared to a subject not having a "s" variant of the 5 HTTLPR polymorphism. Similarly, a subject homozygous for the "l" variant of the 5 HTTLPR polymorphism will be more likely to be a positive responder to therapy with a SRI as compared to a subject having one or more "s" variants of the 5 HTTLPR polymorphism.

Methods of determining a subject's genotype with respect to the 5-HTTLPR region are known in the art and can include, for example, obtaining a biological sample from a patient and testing the sample for the presence of the "s" and/or "l" variant of the 5-HTTLPR region in order to determine genotype at this polymorphism. The sample obtained from the subject can be any biological sample containing nucleic acid, including, for example, blood, urine, skin, hair, sperm, buccal, and tissue samples.

A subject's serotonin transporter gene promoter polymorphism region genotype can be determined using any one of the many techniques known in the art. Methods of genotyping and performing polymerase chain reaction are well known in the art and are not discussed herein in detail. Exemplary techniques include for example, amplification of nucleic acids obtained from a biological sample using the Polymerase Chain Reaction (PCR). The PCR products can be subjected to any method that would allow one to identify the presence of a polymorphism. Exemplary methods, include, for example, subjecting the PCR products to an electrophoretic assay to determine the relative size of the PCR product, probing the PCR products with a nucleic acid sequence specific for a region in the polymorphism, or sequencing the PCR products using techniques known in the art. The detection of polymorphisms can be performed by using restriction enzymes or Single Stranded Conformation Polymorphism (SSCP) techniques. Methods for high throughput detection of nucleotide polymorphisms can be used, including, for example, DNA chip technology. In one embodiment of the present invention, genomic DNA is extracted from whole blood and the 5-HTTLPR region is analyzed by polymerase chain reaction amplification.

The term "GSAD" or generalized social anxiety disorder or generalized social phobia refers to a psychiatric condition in its broadest sense, as defined in American Psychiatric Association: Diagnostic and Statistical Manual of Mental Disorders, Fourth Edition, Washington, D.C., 1994 ("DSM-IV"). The DSM-IV defines "GSAD" as characterized by a marked and persistent fear of one or more social or performance situations in which the person is exposed to unfamiliar people or to possibly scrutiny by others. The DSM-IV sets forth a generally accepted standard for such diagnosing, and categorizing GSAD. Diagnostic features include the following criterion:

TABLE I

| DSM-IV Critereria for diagnosing GSAD | |
|---|---|
| Criterion A | A marked and persistent fear of social or performance situations in which embarrassment may occur. |
| Criterion B | Exposure to the social or performance situation almost invariably provokes an intermediate anxiety response. The anxiety response may take the form of an situationally bound or situationally predisposed Panic Attack. |
| Criterion C | Although adolescents and adults recognize that their fear is excessive or unreasonable, this may not be the case with children. |
| Criterion D | Most often, the social or performance situation is avoided, although it is sometimes endured with dread. |
| Criterion E | The avoidance, fear or anxious anticipation of encountering the social or performance situation has to interfere significantly with the person's daily routine, occupational functioning, or social life, or if the person is markedly distressed about having the phobia. |
| Criterion F | In individuals younger than 18, symptoms must have persisted for at least 6 months before diagnosis. |
| Criterion G | The fear or avoidance is not due to the direct physiological effects of a substance or a general medical condition that it is not better accounted for by another mental disorder. |
| Criterion H | In another medical disorder or general medical condition is present, the fear or avoidance is not limited to concern about its social impact. |

GSAD can be diagnosed and evaluated with any one of several objective, standardized test instruments known in the art, although skilled clinicians can readily diagnose GSAD through unstructured clinical interactions. Standardized test instruments are constructed by experienced clinical researchers based on DSM diagnostic criteria, and are typically validated through statistical studies and comparisons of various patient populations. Generally, standardized instruments assess both manifest psychological or physiological symptoms as well as internal thought processes. Standardized test instruments can comprise structured clinical interviews that are administered by a health care practitioner, or they can comprise self-reporting questionnaires that are completed by the putative patient. Either clinician-administered or self-reported test instruments can be used to identify GSAD patients. Tests for diagnosing GSAD can include, for example the Liebowitz Social Anxiety Disorder Scale (LSAS) (Heimberg et al., *Psychological Medicine* 29:199-212, 1999) and/or the Brief Social Phobia Scale (BSPS) (Davidson et al., *Psychological Medicine* 27:161-166, 1997). In certain embodiments, subjects having GSAD will also be suffering from a second condition, including for example major depression disorder.

SSRIs and noradrenaline-serotonin reuptake inhibitors (NSRIs) are currently the treatment of choice for subjects suffering from GSAD. Methods of treating subjects having GSAD with SSRIs and NSRIs are well known in the art and not discussed herein in detail. Exemplary SSRIs include setraline (registered trademark ZOLOFT™—Pfizer), fluoxetine (registered trademark PROZAC™—Eli Lilly), paroxetine (trade name PAXIL™—Smith Kline Beecham), and fluvoxamine (trade name LUVOX™) and citalopram (trade name CELEXA™.). Exemplary SNRIs include venlafaxine (registered trade name EFFEXOR™ Wyeth) and duloxetine (trade name CYMBALTA™ Eli Lilly).

The present invention provides, inter alia, methods of determining a subject's response profile to SRI treatment. In particular, the present invention provides methods of determining a subject's likely response to SRI treatment. As demonstrated herein, the subject may be a positive responder or poor responder. For use herein, a positive responder, is a subject who positively responds to treatment, i.e., a subject who experiences success in amelioration of GSAD, including any objective or subjective parameter such as abatement; remission; diminishing of symptoms or making the condition more tolerable to the patient; slowing in the rate of degeneration or decline; making the final point of degeneration less debilitating; or improving a subject's physical or mental well-being. A positive responder is one in which any toxic or detrimental side effects of the biologically active agent is outweighed in clinical terms by therapeutically beneficial effects. A poor responder is a subject who responds to treatment but not at the level of the positive responder or a subject who doesn't respond to the treatment at all (i.e., non-responder).

A clinician or other suitable professional can use the information regarding a subject's likely response level to SSRIs or NSRIs to determine an appropriate treatment regimen for the patient. In certain embodiments, if a subject is determined to be a poor responder, a SSRI or NSRI will be administered to the subject at a higher dosage than indicated for positive responders or at a higher dosing frequency than indicated for positive responders. In certain embodiments, subjects that are indicated to be poor responders will receive a different class of drugs before starting treatment with a SSRI or NSRI, during treatment with SSRI or NSRI, and/or following treatment with a SSRI or NSRI (i.e. combination therapy). In certain embodiments, subjects that are indicated to be poor responders will receive only alternative therapies for treating GSAD.

The present invention also provides kits for determining a response profile to treatment with a serotonin reuptake inhibitor in a subject, for determining whether to treat or continue treatment of a subject diagnosed with generalized social anxiety disorder with a serotonin reuptake inhibitor, and/or for optimizing therapeutic efficacy of treatment in a subject diagnosed with generalized social anxiety disorder. The kit will generally comprise reagents necessary for determining a subject's serotonin transporter gene promoter polymorphism genotype and directions for its use. The reagents useful in the kit can be determined by one of skill in the art and can include primers to the appropriate regions of the 5HTT gene in order to amplify nucleic acids from a test sample using PCR. The kit can further include nucleic acid probes useful in determining the presence of the "s" or "l" variant. The kit can also include electrophoretic markers such as a 50 bp ladder. Other components of the kit can include nucleotides, enzymes and buffers useful in a method of the invention. The kit will also include detailed instructions for carrying out the method for detecting subject's serotonin transporter gene promoter polymorphism genotype, i.e., for detecting the presence of the "s" or "l" variant of the 5HTT gene.

From the foregoing description, various modifications and changes in the compositions and methods will occur to those skilled in the art. All such modifications coming within the scope of the appended claims are intended to be included therein. Each recited range includes all combinations and sub-combinations of ranges, as well as specific numerals contained therein.

All publications and patent documents cited above are hereby incorporated by reference in their entirety for all purposes to the same extent as if each were so individually denoted.

Although the foregoing invention has been described in detail by way of example for purposes of clarity of understanding, it will be apparent to the artisan that certain changes and modifications are comprehended by the disclosure and can be practiced without undue experimentation within the scope of the appended claims, which are presented by way of illustration not limitation.

EXAMPLES

Example 1

Determination that the "Long/Short" Polymorphism in the Serotonin Transporter Gene Promoter (5HTTLPR) Influences the Efficacy of Selective Serotonin Reuptake Inhibitors Subjects and Methods The sample consisted of a consecutive series of 32 patients (23 [71.9%] men; 25 [78.1%] Caucasian) ages 19-58 (mean 37.6 sd 9.9) years with GSAD who took an SSRI as part of their participation in randomized controlled trials (RCTs) of SSRIs. Subjects met DSM-IV criteria for a clinically predominant diagnosis of GSAD on the basis of a structured clinical interview (SCID-IV or MINI) by an experienced rater; 6 subjects (18.8%) had comorbid DSM-IV major depressive disorders. The same rater also completed the Liebowitz Social Anxiety Disorder Scale (LSAS) (Heimberg et al., *Psychological Medicine* 29:199-212, 1999) and, in a subset 25 patients, the Brief Social Phobia Scale (BSPS) (Davidson et al., *Psychological Medicine* 27:161-166, 1997) prior to and at the end of 12 weeks of SSRI treatment, and the Clinical Global Impression of Change Scale (CGI-C) (Guy 1976). Mean LSAS score prior to SSRI treatment was 85.4 (sd 23.0). Mean BSPS score prior to SSRI treatment was 42.3 (sd 12.5).

Treatment was with paroxetine (N=27) or fluvoxamine (N=5), at maximally tolerated dose (modal dose 30 mg/d paroxetine or 150 mg/d fluvoxamine). Raters were blind to 5HTTLPR status, which was not determined until after the clinical trials were ended. All subjects gave informed written consent to participate.

Genomic DNA was extracted from whole blood and 5HTTLPR was analyzed by polymerase chain reaction (PCR) amplification, as described elsewhere for the diallelic L-S classification (Gelernter et al., *Hum Genet* 101:243-246, 1997). To genotype the additional SNP that occurs in the VNTR repeat region of the SLC6A4 promoter (Hu et al., *Alcohol Clin Exp Res* 29:8-16, 2005), the same PCR product that can be size fractionated to separate "L" and "S" alleles (without digestion) in MspI (New England Biolabs, Beverly, Mass.) was digested. Undigested, these primers amplify a 410 basepair (bp) segment for the L allele, and a 366 bp segment for the S allele. The A→G substitution (i.e., La→Lg) creates an additional MspI site; there are also two constant MspI sites. After restriction digestion, the digest mixture was size fractionated on agarose gels. Band sizes were 184, 131, 62, and 33 bp for the Lg allele, 315, 62, and 33 bp for the La allele, and 271, 62, and 33 for the S allele. Thus, a single PCR reaction and digest can provide triallelic classification.

Statistical Analysis

PowerMarker (Liu and Muse Bioinformatics 21:2128-2129, 2005. (Free program distributed by the author over the internet from http://www.powermarker.net)) was used to compute exact Hardy Weinberg equilibrium (HWE) statistics. The triallelic genotypes were reclassified into a biallelic model by their level of expression as follows: Lg/S, Lg/Lg, and S/S were reclassified as S'S', La/S and La/Lg were reclassified as L'S', and La/La was reclassified as L'L' (Parsey et al., *Am J Psychiatry* 163:48-51, 2006).

After ensuring that neither clinical response (CGI-C) nor 5HTTLPR genotype (using either the diallelic or triallelic classification) was confounded by sex, ethnicity, or presence of comorbid major depression (Chi-square or Fisher's exact tests, all p values >0.10), we determined whether the number of copies (coded as 0, 1 or 2) of the S allele using the diallelic classification (or the S' allele, using the triallelic classification) predicted dichotomous response status and change in LSAS (and BSPS) scores during SSRI treatment, using logistic and linear regression analyses, respectively.

Results

Distribution of 5HTTLPR alleles for to the diallelic classification was L 53% and S 47%; there was no significant deviation from HWE (chi-square=0.54, df=1, p=0.46). For the triallelic system, the distribution of alleles was La 45%, Lg 8%, and S 47% with no significant deviation from HWE (exact test, p=0.71).

Twenty-one patients (65.6%) were deemed responders to SSRI (i.e., CGI-C much or very much improved). Response rate was predicted by 5HTTLPR genotype at the level of a statistical trend: logistic regression for number of copies of the S allele in the diallelic system, Beta=−1.33 (se 0.68), df=1, p=0.051 (L/L 7/8 [88%], L/S 12/18 [67%], S/S 2/6 [33%]); logistic regression for number of copies of the S' allele in the triallelic classification, Beta=−1.14 (se 0.68), df=1, p=0.093 (L'/L' 4/5 [80%], L'/S' 14/19 [74%], S'/S' 3/8 [38%]) [FIG. 1].

Figure 2:
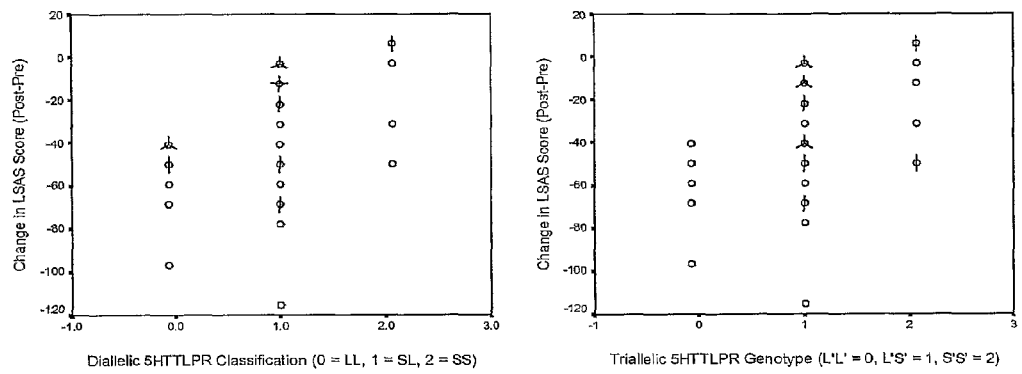
FIG. 2 provides the relationship of 5HTTLPR genotype (diallelic classification on the left; triallelic classification on the right) to change in Liebowitz Social Anxiety Scale (LSAS) scores during 12 weeks of SSRI treatment. Larger negative numbers (i.e., at the bottom of the graph) indicate the greatest reduction in social anxiety symptoms from pre- to post-treatment. The number of "petals" on each "sunflower" indicates the number of individuals with the graphed value.

Reduction in LSAS score during treatment was also significantly predicted by 5HTTLPR genotype: linear regression for number of copies of the S alleles in the diallelic system, adjusted $R^2$=0.176, standardized Beta=0.451, p=0.011; linear regression for number of copies of S' alleles in the triallelic system, adjusted $R^2$=0.195, standardized Beta=0.47%, p 0.008). As can be seen in FIG. 2, the S allele in the diallelic system or the S' allele (i.e., Lg or S) in the triallelic system is associated with poorer response to SSRI treatment (i.e., a smaller reduction in LSAS scores from pre- to post-treatment).

Similarly, in the subjects (N=25) for whom BSPS data were available, change in BSPS score during treatment was also significantly predicted by 5HTTLPR genotype: linear regression for number of copies of S alleles in the diallelic system, adjusted $R^2$=0.206, standardized Beta=0.489, p=0.013; linear regression for number of copies of S' alleles in the triallelic system, adjusted $R^2$=0.180, standardized Beta=0.463, p=0.02) [data not shown].

Discussion

These experiments demonstrate that allelic variation in 5HTTLPR predicts response to SSRIs in patients with GSAD, thereby reinforcing the notion that synaptic (extracellular) serotonin availability is requisite for response.

What is claimed is:

1. A method for determining a response profile to treatment with a serotonin reuptake inhibitor (SRI) in a subject diagnosed with generalized social anxiety disorder comprising determining the subject's serotonin transporter gene promoter polymorphism genotype and predicting the response profile of the subject based on the genotype.

2. The method of claim 1 wherein the serotonin reuptake inhibitor is a selective serotonin reuptake inhibitor (SSRI).

3. The method of claim 1 comprising determining that the subject is homozygous for the long (l) variant of the serotonin transporter gene promoter polymorphism.

4. The method of claim 1 comprising determining that the subject is heterozygous for the long (l) variant of the serotonin transporter gene promoter polymorphism.

5. The method of claim 1 comprising determining that the subject is homozygous for the short (s) variant of the serotonin transporter gene promoter polymorphism.

6. A method for determining whether to treat or continue treatment of a subject diagnosed with generalized social anxiety disorder with a serotonin reuptake inhibitor comprising determining the subject's serotonin transporter gene promoter polymorphism genotype and correlating the subject's serotonin transporter gene promoter polymorphism genotype with a probability of being a positive responder or poor responder to therapy with the serotonin reuptake inhibitor.

7. The method of claim 6 wherein the serotonin reuptake inhibitor is a selective serotonin reuptake inhibitor (SSRI).

8. The method of claim 6 wherein the method is for determining whether to treat a subject diagnosed with generalized social anxiety disorder with a serotonin reuptake inhibitor.

9. The method of claim 6 wherein the method is for determining whether to continue treatment of a subject diagnosed with generalized social anxiety disorder with a serotonin reuptake inhibitor.

10. The method of claim 6 further comprising the step of treating the subject with a serotonin reuptake inhibitor.

11. The method of claim 6 further comprising the step of treating the subject with a therapy for treating generalized social anxiety disorder other than a serotonin reuptake inhibitor.

12. The method of claim 6 wherein the subject is homozygous for the short (s) variant of the serotonin transporter gene promoter polymorphism.

13. The method of claim 12 further comprising the step of treating the subject with a therapy for treating generalized social anxiety disorder other than a serotonin reuptake inhibitor.

14. The method of claim 6 comprising determining whether the subject is heterozygous for the long (l) variant of the serotonin transporter gene promoter polymorphism.

15. The method of claim 14 further comprising the step of treating the subject with a therapy for treating generalized social anxiety disorder other than a selective serotonin reuptake inhibitor.

16. The method of claim 6 comprising determining whether the subject is homozygous for the short (l) variant of the serotonin transporter gene promoter polymorphism.

17. The method of claim 16 further comprising the step of treating the subject with a serotonin reuptake inhibitor.

18. A method for optimizing therapeutic efficacy of treatment in a subject diagnosed with generalized social anxiety disorder comprising determining the subject's serotonin transporter gene promoter polymorphism genotype, correlating the subject's serotonin transporter gene promoter polymorphism genotype with a probability of being a positive responder or poor responder to therapy with a serotonin reuptake inhibitor, and selecting a drug for treatment based on the correlation.

19. The method of claim 18 wherein the serotonin reuptake inhibitor is a selective serotonin reuptake inhibitor (SSRI).

* * * * *